(12) United States Patent
Lopez Villanueva et al.

(10) Patent No.: US 9,834,486 B2
(45) Date of Patent: Dec. 5, 2017

(54) PROCESS FOR PRODUCING HIGH-SWELLABILITY POLYMER COMPOSITES

(71) Applicant: BASF SE, Ludwigshafen (DE)

(72) Inventors: Francisco Javier Lopez Villanueva, Schifferstadt (DE); Tina Mark, Hassloch (DE); Alexandra Wiedemann, Weisenheim am Berg (DE); Alexander Wissemeier, Speyer (DE); Michael Seufert, Bad Duerkheim (DE); Jorge Sanz-Gomez, Heidelberg (DE); Alban Glaser, Mannheim (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 14/787,171

(22) PCT Filed: Apr. 28, 2014

(86) PCT No.: PCT/EP2014/058540
§ 371 (c)(1),
(2) Date: Oct. 26, 2015

(87) PCT Pub. No.: WO2014/177488
PCT Pub. Date: Nov. 6, 2014

(65) Prior Publication Data
US 2016/0075612 A1 Mar. 17, 2016

(30) Foreign Application Priority Data
Apr. 29, 2013 (EP) .................................... 13165864

(51) Int. Cl.
| | |
|---|---|
| *B01J 20/32* | (2006.01) |
| *C05G 3/04* | (2006.01) |
| *C08F 2/44* | (2006.01) |
| *C08F 220/06* | (2006.01) |
| *C08F 2/22* | (2006.01) |
| *A61L 15/60* | (2006.01) |
| *C09K 3/32* | (2006.01) |
| *C09K 17/24* | (2006.01) |
| *C09K 17/48* | (2006.01) |
| *A61L 15/40* | (2006.01) |
| *A62D 1/00* | (2006.01) |
| *C05C 9/00* | (2006.01) |
| *C08J 5/00* | (2006.01) |
| *C09K 17/22* | (2006.01) |
| *C09K 17/32* | (2006.01) |
| *C08F 222/38* | (2006.01) |

(52) U.S. Cl.
CPC ............. *C05G 3/04* (2013.01); *A61L 15/40* (2013.01); *A61L 15/60* (2013.01); *A62D 1/00* (2013.01); *C05C 9/00* (2013.01); *C08F 2/22* (2013.01); *C08F 2/44* (2013.01); *C08F 220/06* (2013.01); *C08J 5/00* (2013.01); *C09K 3/32* (2013.01); *C09K 17/22* (2013.01); *C09K 17/24* (2013.01); *C09K 17/32* (2013.01); *C09K 17/48* (2013.01); *C08F 222/385* (2013.01); *C08J 2333/08* (2013.01)

(58) Field of Classification Search
CPC ....... B01J 20/32; B01J 20/26; B01J 20/28026
USPC ......................................................... 502/402
See application file for complete search history.

(56) References Cited

U.S. PATENT DOCUMENTS

| | | | |
|---|---|---|---|
| 4,076,663 | A | 2/1978 | Masuda et al. |
| 8,883,677 | B2 | 11/2014 | Windhoevel |
| 2004/0234760 | A1 | 11/2004 | Hamed |
| 2009/0163365 | A1 | 6/2009 | Bentlage et al. |
| 2010/0275664 | A1 | 11/2010 | Windhoevel |
| 2014/0294515 | A1 | 10/2014 | Diamantoglou et al. |

FOREIGN PATENT DOCUMENTS

| | | |
|---|---|---|
| CN | 101519476 | 9/2009 |
| DE | 202007016362 | 3/2009 |
| DE | 102007056264 | 7/2009 |
| DE | 102010047379 | 4/2012 |
| JP | S63178115 | 7/1988 |
| JP | 2009242466 | 10/2009 |
| WO | WO 2006119828 | 11/2006 |
| WO | WO 2013060848 | 5/2013 |

OTHER PUBLICATIONS

International Search Report, issued in PCT/EP2014/058540, dated Oct. 9, 2014.
International Preliminary Report on Patentability, issued in PCT/EP2014/058540, dated Jul. 14, 2015.
Product Information [on-line], "KC Flock," Nippon Paper Industries Co., Ltd., Chemical Division, accessed Feb. 16, 2016.

*Primary Examiner* — Edward Johnson
(74) *Attorney, Agent, or Firm* — Brinks Gilson & Lione

(57) ABSTRACT

The invention relates to a process for producing polymer composites suitable for absorbing and storing aqueous liquids, to the polymer composites obtainable by this process, and to the use of the polymer composites. The process comprises free-radical polymerization of a monomer composition M comprising 50 to 100% by weight, based on the total amount of monomers A and B, of at least one monomer A having one ethylenic double bond and at least one neutralizable acid group, 0 to 50% by weight of optionally one or more comonomers B which are different than the monomers A and have one ethylenic double bond, and 1 to 10% by weight, based on the total amount of monomers A and B, of at least one crosslinker C.

14 Claims, No Drawings

PROCESS FOR PRODUCING HIGH-SWELLABILITY POLYMER COMPOSITES

This application is a National Stage application of International Application No. PCT/EP2014/058540, filed Apr. 28, 2014. This application also claims priority under 35 U.S.C. §119 to European Patent Application No. 13165864.3, filed Apr. 29, 2013.

The present invention relates to a process for producing polymer composites suitable for absorbing and storing aqueous liquids, and to the polymer composites obtainable by this process. The invention also relates to the use of these polymer composites.

Polymers suitable for absorbing and storing several times their own weight of aqueous liquids are known. For such polymers, names such as "superabsorbent", "high-swellability polymer", "hydrogel" (often also used for the dry form), "hydrogel-forming polymer", "water-absorbing polymer", "absorbent gel-forming material", "swellable resin", "water-absorbing resin", "water-absorbing polymer" or the like are also commonly used. These polymers are crosslinked hydrophilic polymers, more particularly polymers formed from (co)polymerized hydrophilic monomers, graft (co)polymers of one or more hydrophilic monomers on a suitable graft base, crosslinked cellulose ethers or starch ethers, crosslinked carboxymethylcellulose, partly crosslinked polyalkylene oxide or natural products swellable in aqueous liquids, for example guar derivatives, the most common being polymers based on partly neutralized acrylic acid. The essential properties of such polymers are their abilities to absorb several times their own weight of aqueous liquids and not to release the liquid again even under a certain pressure. High-swellability polymers of this kind, which are typically used in the form of a dry powder, are converted to a gel when they absorb fluid, and correspondingly to a hydrogel when they absorb water as usual. Crosslinking is essential for synthetic high-swellability polymers and is an important difference from customary straightforward thickeners, since it leads to the insolubility of the polymers in water.

Fredric L. Buchholz and Andrew T. Graham (editors), in: "Modern Superabsorbent Polymer Technology", J. Wiley & Sons, New York, U.S.A./Wiley-VCH, Weinheim, Germany, 1997, ISBN 0-471-19411-5, give a comprehensive review of high-swellability polymers, the properties thereof and processes for producing high-swellability polymers.

High-swellability polymers of a wide variety of different types have now developed to become an economically very important group of products, and there are enormous global production capacities. As well as the current principal use in the hygiene sector, other fields of use are also gaining significance, for example as soil amendments in agriculture and in horticulture, or as fire extinguishants, to mention just a few.

US 2004/0234760 A1 describes the production of water-swellable cellulose fibers, in which conventional cellulose fibers are impregnated with an aqueous solution of a carboxyl-containing monomer and a crosslinker, and then the monomers are polymerized fully to give a water-swellable polymer.

WO 2006/119 828 A1 teaches a polymer composite material formed from high-swellability polymers based on crosslinked polyacrylates and inorganic solid particles, which is suitable as a plant substrate. The production is effected by free-radical polymerization of acrylic acid in the presence of crosslinkers.

DE 102007056264 describes a polymer composite material for improving soil quality, especially for increasing water absorption capacity and water storage capacity of soils, that comprises a water-swellable polymer as the matrix and inorganic solid particles distributed in the matrix, the polymer having carbohydrate-based structural units. The material is produced by free-radical polymerization of a mixture of at least partly neutralized acrylic acid, crosslinkers, inorganic particles and soluble carbohydrates.

CN 101519476 describes a process for preparing water-absorbing graft polymers, which includes polymerization of a propenyl monomer such as sodium acrylate and acrylamide in an aqueous solution of cellulose which contains sodium hydroxide and urea.

One disadvantage of the high-swellability polymers based on acrylic acid known from the prior art is in many cases the very poor or even absent biodegradability and compostability, which is of significance especially when the high-swellability polymers are to be used for improving soil quality, especially for improving the absorption and storage of water in soils.

The industrial plants for production of the high-swellability polymers known from the prior art are often very costly and entail extensive investment in apparatus, control technology, energy supply, whether for heating or cooling, stirring etc. The space required for such plants is usually also very large. High costs also arise in many cases for the transport of the starting materials.

There is thus a need here for improved products and for processes which work better and more advantageously and which lead to high-swellability polymers which have a good and improved profile of properties, and which allow the processing of many substances, more particularly of often worthless waste products, and hence also enable disposal problems at source, and even then are still environmentally friendly and additionally offer better utility and new applications.

DE 102010047379 describes compostable water-absorbing and water-storing polymer composite materials based on acrylic acid, which comprise waste materials based on polysaccharides, especially based on lignin-containing cellulose materials, and which have good biodegradability and good compostability. The polymers are prepared by free-radical polymerization of an aqueous mixture of acrylic acid, crosslinker, waste material and water under acidic conditions, followed by a neutralization of the reaction product. Firstly, problems arise here in the performance of the process. In addition, the content of unconverted monomers is very high, especially when the polymerization is performed in the presence of water-insoluble lignin-containing cellulose materials. Another disadvantage is found to be the neutralization which follows the polymerization, since relatively large amounts of solvent and water are required for this purpose, and then have to be removed again, which results in additional procedural complexity and expenditure.

Earlier filed patent application PCT/EP2012/071269 (published as WO 2013060848) describes a process similar to that of DE 102010047379, which avoids some of the problems of DE 102010047379 by using urea.

It is therefore an object of the invention to provide high-swellability polymer composites which can absorb and store aqueous liquids such as water, solutions, emulsions and liquid dispersions, and are simultaneously compostable and can therefore be used to improve soil quality. More particularly, the high-swellability polymer composites are to have good water absorption capacity and are to be very substantially or fully degraded in the soil. It is also a further object of the invention to provide a process for producing such products, which is simple and economically viable to perform, which does not require any great apparatus complexity, which is environmentally friendly, and in which it is possible to use cheap waste products and by-products which often cannot be reutilized in any other way without great cost and inconvenience. The process is additionally to lead in high yield and reliably to good and versatile products with a comparatively low content of unconverted monomers. In addition, the process should also be performable without a subsequent neutralization step.

These and further objects are achieved by the process described in the claims and hereinafter, and by the high-swellability polymer composites obtainable thereby.

Accordingly, the invention relates to a process for producing polymer composites suitable for absorbing and storing aqueous liquids, comprising free-radical polymerization of a monomer composition M which comprises
a) 50 to 100% by weight, based on the total amount of monomers A and B, of at least one monomer A having one ethylenic double bond and at least one neutralizable acid group,
b) 0 to 50% by weight of optionally one or more comonomers B which are different than the monomers A and have one ethylenic double bond, and
c) 0 to 10% by weight, based on the total amount of monomers A and B, of at least one crosslinker C,
wherein the polymerization of the monomer composition is performed in an aqueous suspension of a water-insoluble particulate substance S comprising cellulose or lignocellulose, the weight ratio of the monomer composition M to the substance S being in the range from 9:1 to 1:9; and
wherein the monomers A used for polymerization are present in the aqueous suspension in neutralized, i.e. anionic, form to an extent of at least 10 mol %, frequently to an extent of at least 20 mol %, particularly to an extent of at least 30 mol %, more particularly to an extent of at least 35 mol-% and especially to an extent of at least 50 mol %.

The process according to the invention gives, in a reliable and easily performable manner, high-swellability polymer composites, i.e. composite materials composed of the polymers obtained in the polymerization of the monomer composition and the substance S, which can absorb and store several times their own weight of aqueous liquids. The composite materials after drying are free-flowing and have a low residual monomer content. The process gives the composite materials in very high yields, based on the feedstocks, and can also be performed without subsequent neutralization.

A particularly advantageous possibility is that of using waste materials and by-products obtained in the processing of polysaccharide-containing materials, without any adverse effect thereof on the quality of the polymers obtained. These can be processed without any problems directly at the location and site where they are obtained. This dispenses with disposal of the waste materials and by-products; the polymers obtained in accordance with the invention are very environmentally friendly.

In addition, the materials are compostable and are substantially or fully degraded in the soil. The composite materials are particularly suitable for improving the soil quality of agriculturally utilized soils and particularly promote the growth, especially the root growth, of the plants grown therein. In this way, these materials allow an increased yield.

The use obtainable in accordance with the invention as soil improvers compost the polymers over the course of time, but continue to work for such a period that they can fulfill their task, for example as a water sponge, for a couple of years. This is also true when they are used filled with fertilizers or crop protection compositions and the like. In this respect, they are also very suitable for the controlled release of water and active ingredients.

The invention also provides the polymer composites obtainable by the process according to the invention.

In the process according to the invention, a free-radical polymerization of a monomer composition M is performed in the presence of at least one water-insoluble particulate cellulose- or lignocellulose-based substance S.

The monomer composition M comprises at least 50% by weight, particularly at least 70% by weight and especially at least 80% by weight or at least 90% by weight of one or more monomers A having one polymerizable ethylenic double bond and at least one, especially one or two, neutralizable acid group(s).

The acid group of the monomers A may, for example, be a carboxyl, sulfo or phosphonic acid group. Preferably, the monomers A comprise at least one monoethylenically unsaturated monomer which acid group has exclusively one or two carboxyl groups. Preferably, the monomers A comprise at least one monoethylenically unsaturated monomer having exclusively one or two carboxyl groups as the acid group (monomer A1). More particularly, monomer A comprises, as the main constituent, i.e. to an extent of more than 50% by weight, based on the total amount of the monomers A, one or more monomers A1. Preferred monomers A1 have one carboxyl group and one ethylenic double bond. In a specific embodiment, the monomers A are selected exclusively or to an extent of at least 95% from monomers A1. In another embodiment, the monomers A comprise 50% by weight to 99.9% by weight, especially 60 to 99.5% by weight, based on the total amount of the monomers A, of one or more monomers A1 and 0.1 to 50% by weight, especially 0.5 to 40% by weight, of one or more monomers A having at least one acid group other than a carboxyl group for example a sulfo group or phosphonic acid group.

In general, the monomers A are water-soluble, i.e. the solubility in water at 23° C. is typically at least 1 g/100 g of water, preferably at least 5 g/100 g of water, more preferably at least 25 g/100 g of water and most preferably at least 35 g/100 g of water.

Suitable monomers A are especially
monoethylenically unsaturated monocarboxylic acids having 3 to 8 carbon atoms, hereinafter monoethylenically unsaturated $C_3$-$C_8$-monocarboxylic acids, for example acrylic acid, methacrylic acid and ethacrylic acid, and mixtures thereof;
monoethylenically unsaturated dicarboxylic acids having 4 to 8 carbon atoms, hereinafter monoethylenically unsaturated $C_4$-$C_8$-dicarboxylic acids, such as maleic acid, fumaric acid and itaconic acid, and mixtures thereof;
monoethylenically unsaturated sulfonic acids, such as styrenesulfonic acid and 2-acrylamido-2-methylpropanesulfonic acid (AMPS);
monoethylenically unsaturated phosphonic acids, such as vinylphosphonic acid.

Preferred monomers A are selected from monoethylenically unsaturated $C_3$-$C_8$-monocarboxylic acids, especially from acrylic acid and methacrylic acid, mixtures thereof and mixtures of at least one monoethylenically unsaturated $C_3$-$C_8$-monocarboxylic acid such as acrylic acid or methacrylic acid with one or more monoethylenically unsaturated $C_4$-$C_8$-dicarboxylic acids such as itaconic acid.

More particularly, the monomers A are selected from monoethylenically unsaturated $C_3$-$C_8$-monocarboxylic acids, especially from acrylic acid and methacrylic acid.

The proportion of acrylic acid in the total amount of monomers A is especially at least 50% by weight, more preferably at least 90% by weight, most preferably at least 95% by weight.

According to the invention, the monomers A in the aqueous suspension used for polymerization are in at least partly neutralized form, i.e. at least some of the monomers A are in the form of the acid anion ions or in deprotonated form. Suitable counterions to maintain charge neutrality are particularly alkali metal ions such as sodium and potassium ions, and also ammonium ions ($NH^{4+}$). More preferably, the neutralized monomers A are in the form of their sodium or potassium salts. Especially, the neutralized monomers A are in the form of their potassium salts. According to the invention, the neutralization level is at least 10% and may be up to 100%, meaning that at least 10 mol % of the monomers present in the aqueous suspension are in neutralized, i.e. anionic, form. Frequently, the neutralization level is at least 20%, particularly at least 30% or at least 35% and especially at least 50%, and is preferably in the range from 20 to 90%, particularly in the range from 30 to 90% or from 30 to 85% and especially in the range from 35 to 80% or from 50 to 80%.

The neutralization level of the monomers A used for polymerization can be adjusted by treating the monomers A, preferably an aqueous solution of the monomers A, with at least one suitable base, for example ammonia, sodium hydroxide or especially potassium hydroxide, preferably with an aqueous solution of at least one such base. The amount of base is selected such that the desired neutralization level is attained. Alternatively, the neutralization level can also be adjusted such that already neutralized monomer A, i.e. a suitable salt of the monomer A, for example a sodium, potassium or ammonium salt of the monomer A or a mixture of at least one such salt with at least one non-neutralized monomer A in such a molar ratio that corresponds to the desired neutralization level. In this case, the neutralized and non-neutralized monomers A may be the same or different.

As well as the monomers A, the monomer composition may comprise monoethylenically unsaturated monomers which are different than the monomers A and are copolymerizable with the monomers A (comonomers B).

In general, the monomers B are water-soluble, i.e. the solubility in water at 23° C. is typically at least 1 g/100 g of water, preferably at least 5 g/100 g of water, more preferably at least 25 g/100 g of water and most preferably at least 35 g/100 g of water.

Suitable comonomers B are, for example,
primary amides of monoethylenically unsaturated $C_3$-$C_8$-monocarboxylic acids, such as acrylamide or methacrylamide,
hydroxy-$C_2$-$C_4$-alkyl esters, especially 2-hydroxyethyl esters, of monoethylenically unsaturated $C_3$-$C_8$-monocarboxylic acids, such as hydroxyethyl acrylate, hydroxyethyl methacrylate,
monomers bearing amino groups, especially di-$C_1$-$C_4$-alkylamino-$C_2$-$C_4$-alkyl esters and di-$C_1$-$C_4$-alkylamino-$C_2$-$C_4$-alkylamides of monoethylenically unsaturated $C_3$-$C_8$-monocarboxylic acids, such as dimethylammonioethyl methacrylate, dimethylaminoethyl acrylate, dimethylaminopropyl acrylate, diethylaminopropyl acrylate, dimethylaminoethyl methacrylate, diethylaminoethyl methacrylate, dimethylaminoethyl-methacrylamide, dimethylaminoethylacrylamide, dimethylaminopropylacrylamide, diethylaminopropylacrylamide, dimethylaminoethylmethacrylamide and diethylaminoethylmethacrylamide;
monomers bearing quaternary ammonium groups, especially tri-$C_1$-$C_4$-alkylammonio-$C_2$-$C_4$-alkyl esters and tri-$C_1$-$C_4$-alkylammonio-$C_2$-$C_4$-alkylamides of monoethylenically unsaturated $C_3$-$C_8$-monocarboxylic acids, especially the chlorides or sulfates thereof, such as trimethylammonioethyl methacrylate, trimethylammonioethyl acrylate, trimethylammoniopropyl acrylate, trimethylammoniopropyl acrylate, triethylammonioethyl methacrylate, triethylammonioethyl methacrylate, trimethylammonioethylmethacrylamide, trimethylammonioethylacrylamide, trimethylammoniopropylacrylamide, trimethylammoniopropylacrylamide, triethylammonioethylmethacrylamid and triethylammonioethylmethacrylamide;
monoethylenically unsaturated mononitriles having 3 to 8 carbon atoms, such as acrylonitrile and methacrylonitrile; and
anhydrides monoethylenically unsaturated dicarboxylic acids having 4 to 8 carbon atoms, hereinafter anhydrides monoethylenically unsaturated $C_4$-$C_8$-dicarboxylic acids, such as maleic anhydride.

The comonomers B account for generally not more than 50% by weight, particularly not more than 30% by weight and especially not more than 20% by weight, based on the total amount of monomer A+comonomer B.

In a preferred embodiment, the monomer composition does not comprise any comonomer B bearing an amino group or a quaternary ammonium group, or comprises less than 1% by weight of such a comonomer B, based on the total weight of monomer A+comonomer B.

In a specific embodiment, the monomer composition does not comprise any comonomer B or comprises less than 1% by weight of comonomers B, based on the total weight of the monomer composition, i.e. based on the total amount of monomer A+comonomer B+crosslinker C.

As well as the monomers A and any comonomer B present, the monomer composition optionally comprises up to 10% by weight, particularly to 5% by weight, particularly to 2% by weight, for example 0.01 to 10% by weight, frequently 0.05 to 5% by weight or 0.1 to 2% by weight, based on the total amount of monomer A and any comonomer B present, of one or more crosslinkers C. In a preferred embodiment of the invention, the monomer composition comprises essentially no crosslinker C, i.e. the amounts of crosslinker C are less than 0.1% by weight, particularly less than 0.05% by weight and especially less than 0.01% by weight, based on the total amount of monomers A and any comonomer B present.

The crosslinkers used may in principle be all substances comprising either at least two ethylenically unsaturated groups or at least one ethylenic double bond and at least one functional group which reacts with acid groups or at least two functional groups which react with acid groups. The reaction of the functionality may include formation of a covalent bond or of a coordinate bond.

Crosslinkers C are preferably compounds having at least two, e.g. 2, 3, or 4 polymerizable groups which can be polymerized free-radically into the polymer network. Suitable crosslinkers C are, for example, acrylate esters and methacrylate esters of organic aliphatic polyols having at least two, e.g. 2, 3 or 4 hydroxyl groups such as ethylene glycol dimethacrylate, diethylene glycol diacrylate, polyethylene glycol diacrylate, trimethylolpropane triacrylate, tetraallyloxyethane, as described in EP 530 438 A1, di- and triacrylates, as described in EP 547 847 A1, EP 559 476 A1, EP 632 068 A1, WO 93/21237 A1, WO 2003/104299 A1, WO 2003/104300 A1, WO 2003/104301 A1 and DE 103 31 450 A1, mixed acrylates which, as well as acrylate groups, comprise further ethylenically unsaturated groups, as described in DE 103 31 456 A1 and DE 103 55 401 A1, allyl esters of acrylic or methacrylic acid such as allyl methacrylate, methylenebisacrylamide, methylenebismethacrylamide, or crosslinker mixtures as described, for example, in DE 195 43 368 A1, DE 196 46 484 A1, WO 90/15830 A1 and WO 2002/32962 A2. In addition, it is possible to use crosslinkers including diallylacrylamide, triallyl citrate, allyl ethers of di- and polyols and ethoxylates thereof, such as pentaerythrityl triallyl ether or tetraallyloxyethane, and allyl ethers of amines and salts thereof, these having at least two ethylenic double bonds, for example triallylamine and tetraallylammonium chloride.

Preferred crosslinkers C are pentaerythrityl triallyl ether, tetraallyloxyethane, methylenebisacrylamide, methylenebismethacrylamide, 10- to 20-tuply ethoxylated trimethylolpropane triacrylate, 10- to 20-tuply ethoxylated trimethylolethane triacrylate, more preferably 15-tuply ethoxylated trimethylolpropane triacrylate, polyethylene glycol diacrylates having 4 to 30 ethylene oxide units in the polyethylene glycol chain, trimethylolpropane triacrylate, di- and triacrylates of 3- to 30-tuply ethoxylated glycerol, more preferably di- and triacrylates of 3- to 20-tuply ethoxylated glycerol, and triallylamine. The polyols incompletely esterified with acrylic acid may also be present here as Michael adducts with one another, as a result of which it is also possible for tetraacrylates, pentaacrylates or even higher acrylates to be present. In a particularly preferred embodiment of the present invention, the crosslinker C used is methylenebisacrylamide.

Even more preferred crosslinkers are acrylate and methacrylate esters of plyethylenylene oxide or of ethoxylated aliphatic polyols having 2, 3, 4 or 5 hydroxyl groups such as 10- to 20-tuply ethoxylated trimethylolpropane triacrylate, 10- to 20-tuply ethoxylated trimethylolethane triacrylate, more preferably 15-tuply ethoxylated trimethylolpropane triacrylate, polyethylene glycol diacrylates having 4 to 30 ethylene oxide units in the polyethylene glycol chain, di- and triacrylates of 3- to 30-tuply ethoxylated glycerol, more preferably di- and triacrylates of 3- to 20-tuply ethoxylated glycerol.

As well as the monomer A, any comonomer B present and the crosslinker C, the monomer composition typically comprises no or not more than 1% by weight of ethylenically unsaturated compounds other than the monomer A, any comonomer B present and the crosslinker C. In other words: the monomer A, any comonomer B present and the crosslinker C form the polymer in the polymerization.

According to the invention, the monomer composition is polymerized in an aqueous suspension of the substance S.

The polysaccharide-comprising substance S is typically used in such an amount that the weight ratio of substance S to the monomer composition M, i.e. to the total amount of monomer A+any comonomer B present+any crosslinker C present, is in the range from 1:9 to 9:1, preferably in the range from 2:8 to 8:2, particularly in the range from 7:3 to 3:7 and especially in the range form 1:2 to 2:1. In this way, a balanced ratio of water absorption capacity and compostability/biodegradability in the soil is achieved. It is assumed that, under the polymerization and/or drying conditions, particularly efficient binding/grafting of the polymer formed from the monomers of the monomer composition to the polysaccharide molecules present in the particles of the substance S is achieved.

The substance S used may in principle be all cellulosic or lignocellulosic materials. More particularly, the substance S consists essentially, i.e. to an extent of at least 80% by weight or to an extent of at least 90% by weight, of cellulose or lignocellulose or mixtures thereof.

According to the invention, the substances S are water-insoluble, i.e. the water solubility is below 1 g per liter at 20° C.

Preference is given to using the substance S in the form of a finely divided particulate material. "Finely divided" is understood to mean that at least 90% by weight of the particles of the material have particle dimensions below 1 mm, particularly not more than 900 µm and especially not more than 800 µm. More particularly, at least 90% by weight of the particles have dimensions in the range from 1 to <1000 µm, particularly in the range from 5 to 800 µm and especially in the range from 10 to 800 µm, determined by sieve analysis.

The particulate materials may be of regular or irregular shape, compact or porous, where spherical, ellipsoidal, rod-shaped or fibrous be. "Fibrous" is understood to mean, i.e. the ratio of length to thickness is at least 5:1. Is. Spherical particles generally have a ratio of length to thickness of not more than 1.5:1, whereas rod-shaped and ellipsoidal particles have a ratio of length to thickness in the range from >1.5:1 to <5:1. Preferably, at least a portion of the substance S is in fibrous form, particularly at least 10% by weight and especially at least 20% by weight of the substance S.

Preferably, the substance S comprises at least one cellulosic substance which comprises bound lignin, and these are also referred to as lignocellulose materials. These include particularly materials of vegetable origin, such as finely divided materials based on wood and plant parts, e.g. hemp dust, flax dust, sawdust, bran, ground straw, ground olive stones, ground tree bark, sugar beet peel, sugar cane waste, rice husks, cereal husks, ground hemp fibers, ground flax fibers, ground Chinese silvergrass fibers, ground coconut fibers, ground kenaf fibers or ground wood fibers, including pulp or mechanical pulp from papermaking. These particularly also include industrial waste materials comprising cellulose and lignin, for example reject materials from pulp production and waste materials from biogas production. Preference is given to substances S comprising essentially only lignocellulose materials, and mixtures of lignocellulose materials with lignin-free or low-lignin cellulose materials. Examples of lignin-free and low-lignin cellulose materials are pulp, including chemical and chemo-thermomechanical pulp, raw cellulose and purified cellulose, including microcrystalline cellulose, fibrilated and microfibrilated cellulose.

In preferred embodiments, the proportion of ligneous materials is at least 50% by weight, particularly at least 60% by weight, based on the total mass of the substance S. In specific embodiments of the invention, the ligneous materials account for at least 90% by weight, based on the total mass of the substance S. In other specific embodiments, the substance S is a mixture of at least one lignocellulose material with at least one lignin-free or low-lignin cellulose material. In these mixtures, the lignocellulose materials account for typically 50 to 90% by weight and particularly 60 to 85% by weight, and the lignin-free or low-lignin cellulose materials for 10 to 50% by weight and particularly 15 to 40% by weight, based on the total weight of the substance S.

In particularly preferred embodiments, the ligneous cellulose materials are vegetable or industrial waste materials or by-products obtained in the processing and treatment of vegetable materials, or mixtures thereof with lignin-free or low-lignin cellulose materials, in which case the proportion of waste materials or by-products accounts for preferably at least 50% by weight and particularly at least 60% by weight, based on the total mass of the substance S. In very particularly preferred embodiments of the invention, the waste materials or by-products account for at least 90% by weight, based on the total mass of the substance S. In further particularly preferred embodiments, the substance S is a mixture of at least one ligneous industrial or vegetable waste material with at least one lignin-free or low-lignin cellulose material. In these mixtures, the waste materials account for typically 50 to 90% by weight and particularly 60 to 85% by weight, and the lignin-free or low-lignin cellulose materials for 10 to 50% by weight and particularly 15 to 40% by weight, based on the total weight of the substance S.

Examples of such vegetable or industrial waste materials or by-products obtained in the processing and treatment of vegetable materials are, without any restriction thereto, hemp dust, flax dust, sawdust, ground straw, ground olive stones, ground tree bark, reject material from pulp production, waste materials from biogas production, sugar beet peel, sugar cane waste, rice husks, cereal husks, ground hemp fibers, ground flax fibers, ground Chinese silvergrass fibers, ground coconut fibers, ground kenaf fibers and ground wood fibers, the vegetable or industrial waste materials or by-products particularly being in the form of a finely divided material having the above-specified particle sizes.

In likewise particularly preferred embodiments of the invention, the substance S is a vegetable waste material such as hemp dust or flax dust, or a mixture thereof with pure cellulose or raw cellulose, in which case the proportion of hemp dust or flax dust is preferably at least 50% by weight, particularly at least 60% by weight or at least 90% by weight, based on the total mass of the substance S. In further particularly preferred embodiments, the substance S is a mixture of at least one ligneous vegetable waste material with at least one lignin-free or low-lignin cellulose material. In these mixtures, the waste materials account for typically 50 to 90% by weight and particularly 60 to 85% by weight, and the lignin-free or low-lignin cellulose materials for 10 to 50% by weight and particularly 15 to 40% by weight, based on the total weight of the substance S.

According to the invention, the polymerization of the monomer composition is performed in an aqueous suspension of the substance S, i.e. the substance S is suspended in an aqueous liquid at least during the polymerization. The aqueous liquids include, as well as water, also solvent-water mixtures, but these may generally comprise up to 10% by weight, based on the aqueous liquid, of organic water-miscible solvents, e.g. alcohols such as methanol or ethanol. Preferably, the aqueous liquid is water comprising no or not more than 5% by weight and particularly not more than 2% by weight of organic solvents.

By using the aqueous liquid, it is possible to impart an initial viscosity advantageous for the performance of the reactions to the system, i.e. to the reaction mixture. Typically, the initial viscosity (determined to DIN EN 2555-2000 by means of a Brookfield viscometer at 23° C. at a shear gradient of <10 sec$^{-1}$) in the range from 10 to 2000 mPa·s, in particular from 10 to 1000 mPa·s. Typically, the reaction mixture is dilatant, i.e. has a higher viscosity at a low shear rate of <10 sec$^{-1}$ and a lower viscosity at a higher shear rate (>100 sec$^{-1}$).

The initial viscosity of the reaction mixture prior to the polymerization can be adjusted in a simple manner via the amount of the feedstocks and of the aqueous liquid. Preferably, the total amount of substance S and monomer composition is 10 to 80% by weight, particularly 20 to 70% by weight and particularly 30 to 60, based on the total amount of the reaction mixture, i.e. based on the total amount of substance S, monomer composition and aqueous liquid. Preferably, the amount of substance S is 5 to 50% by weight and particularly 5 to 40% by weight, based on the total amount of the reaction mixture, i.e. based on the total amount of substance S, monomer composition and aqueous liquid.

According to the invention, the polymerization is performed by free-radical means. Processes for this purpose are basically known, for example from Fredric L. Buchholz and Andrew T. Graham (eds.) "Modern Superabsorbent Polymer Technology", J. Wiley & Sons, New York, U.S.A./Wiley-VCH, Weinheim, Germany, 1997, chapters 2 and 3 and literature cited therein.

Polymerization by free-radical means that the polymerization is performed under conditions where free radicals are generated. Free radicals may be generated by irradiation of the reaction mixture, i.e. the aqueous suspension of the particulate substance S containing the monomer composition M, or by adding one or more polymerization initiators to the reaction mixture for this purpose and optionally heating the reaction mixture to the polymerization temperature The polymerization initiators used may be all compounds which generate free radicals under the polymerization conditions, for example thermal initiators, redox initiators or photoinitiators. Preference is given to thermal initiators, especially to those having a peroxide group or azo-initiators, and to redox initiators. Suitable thermal initiators are especially the salts of peroxodisulfuric acid, such as sodium peroxodisulfate, potassium peroxodisulfate and ammonium peroxodisulfate. Suitable thermal initiators also include azo-initiators, such as 2,2'-azobisisobutyronitrile, 2,2'-azobis(2-methylbutyronitrile), 2,2'-azobis[2-methyl-N-(–2-hydroxyethyl)propionamide], 1,1'-azobis(1-cyclohexanecarbonitrile), 2,2'-azobis(2,4-dimethylvaleronitrile), 2,2'-azobis(N,N'-dimethyleneisobutyroamidine)dihydrochloride, and 2,2'-azobis(2-amidinopropane)dihydrochloride. Suitable redox initiators are particularly peroxides in combination with one or more reducing agents. Examples of peroxides are hydrogen peroxide and the aforementioned salts of peroxodisulfuric acid. Examples of reducing agents are ascorbic acid, sodium bisulfite, salts of 2-hydroxy-2-sulfinatoacetic acid and salts of 2-hydroxy-2-sulfonatoacetic acid, especially the sodium salts, and mixtures of the reducing agents. Examples of redox initiator systems are sodium peroxodisulfate/ascorbic acid, hydrogen peroxide/ascorbic acid, sodium peroxodisulfate/sodium bisulfite and hydrogen peroxide/sodium bisulfite. In one embodiment of the invention, mixtures of thermal initiators and redox initiators, in particular a mixture of a salt of peroxodisulfuric acid and a redox initiator are used, such as sodium peroxodisulfate/hydrogen peroxide/ascorbic acid. Likewise suitable are combinations of thermal initiators and redox initiators which comprise a salt of peroxodisulfuric acid and a redox initiator, wherein the reducing component used is a mixture of the sodium salt of 2-hydroxy-2-sulfinatoacetic acid, the disodium salt of 2-hydroxy-2-sulfonatoacetic acid and sodium bisulfite (in the form of Brüggolit® FF6M or Brüggolit® FF7, or alternatively BRUGGOLITE® FF6M or BRUGGOLITE® FF7, available from L. Brüggemann KG, Salzstrasse 131, 74076 Heilbronn, Germany, www.brueggemann.com). In another embodiment, the initiator is a thermal initiator, preferably a salt of peroxodisulfuric acid, such as sodium peroxodisulfate, potassium peroxodisulfate and ammonium peroxodisulfate.

The total amount of polymerization initiator will generally be from 0.3 to 6% by weight, in particular from 0.4 to 5% by weight, in particular form 0.5 to 4% by weight, especially from 1 to 3% by weight, based on the total weight of monomers A and B.

While it is principally possible to perform the polymerization reaction in the presence of a single type of polymerization initiator, in particular in the presence of a single type of thermal polymerization initiator, especially in the presence of a salt of peroxodisulfuric acid, such as sodium peroxodisulfate, potassium peroxodisulfate and ammonium peroxodisulfate, it is beneficial, if the polymerization is performed in the presence of a combination of at least two different polymerization initiators. Hence, in a preferred embodiment the aqueous suspension contains at least two different polymerization initiators. In this context, the phrase "different of polymerization initiator" is understood as "different types of polymerization initiator". Different types may be different types of thermal polymerization initiators, different types of redox initiators or the combination of a thermal initiator and a redox initiator. When different types of polymerization initiators, the decomposition temperatures of the different types of polymerization initiators, i.e. the temperature above which the polymerization initiator decomposes and forms the initiating radicals, is preferably distinct by at least 10 K, in particular by at least 20 K, e.g. by 10 to 100 K or by 20 to 70 K.

In a particular embodiment of the invention, the polymerization is carried out in the presence of a thermal polymerization initiator and a redox polymerization initiator. In this embodiment, the thermal polymerization initiator is preferably a salt of peroxodisulfuric acid, such as sodium peroxodisulfate, potassium peroxodisulfate and ammonium peroxodisulfate. In this embodiment, the redox polymerization initiator is preferably a combination of hydrogen peroxide and a reducing agent, in particular a combination of hydrogen peroxide and ascorbic acid. In this embodiment the amount of thermal polymerization initiator, in particular the amount of the salt of peroxodisulfuric acid, is frequently in the range from 0.2 to 5% by weight, in particular from 0.5 to 3% by weight, especially from 0.8 to 1.6% by weight, based on the total weight of monomers A and B. In this embodiment the amount of redox initiator, in particular the total amount of $H_2O_2$ and reducing agent, e.g. ascorbic acid, is frequently in the range from 0.02 to 1.2% by weight, in particular from 0.1 to 0.7% by weight, especially from 0.12 to 0.5% by weight, based on the total weight of monomers A and B. If the oxidizing agent of the redox initiator is $H_2O_2$, the amount of $H_2O_2$ is in particular from 0.01 to 0.5% by weight, especially from 0.05 to 0.2% by weight, based on the total weight of monomers A and B. If the reducing agent of the redox initiator is ascorbic acid, the amount of ascorbic acid is in particular from 0.01 to 0.7% by weight, especially from 0.07 to 0.3% by weight, based on the total weight of monomers A and B.

In another particular embodiment of the invention, the polymerization is carried out in the presence of a first thermal polymerization initiator and a second thermal polymerization initiator having a lower decomposition temperature than the first thermal polymerization initiator. In this embodiment, the first thermal polymerization initiator is preferably a salt of peroxodisulfuric acid, such as sodium peroxodisulfate, potassium peroxodisulfate and ammonium peroxodisulfate. In this embodiment, the second thermal polymerization initiator is preferably an azo compound, in particular a water-soluble azo compound, such as 2,2'-azobis [2-methyl-N-(-2-hydroxyethyl)-propionamide], 2,2'-azobis (N,N'-dimethyleneisobutyroamidine)dihydrochloride, and 2,2'-azobis(2-amidinopropane)dihydrochloride. In this embodiment the amount of first thermal polymerization initiator, in particular the amount of the salt of peroxodisulfuric acid, is frequently in the range from 0.2 to 5% by weight, in particular from 0.5 to 3% by weight, especially from 0.8 to 1.6% by weight, based on the total weight of monomers A and B. In this embodiment the amount of second thermal polymerization initiator, in particular the azo compound, is frequently in the range from 0.05 to 1.0% by weight, in particular from 0.1 to 0.7% by weight, especially from 0.2 to 0.5% by weight, based on the total weight of monomers A and B.

The polymerization can be performed in the presence of a hydroquinone monoether as a chain transfer agent/modulator. The reaction mixture comprises preferably at most 250 ppm by weight, more preferably at most 130 ppm by weight, especially preferably at most 70 ppm by weight, of hydroquinone monoether, based in each case on monomer A. If desired, the content in the monomer composition of hydroquinone monoether is frequently at least 10 ppm by weight, particularly at least 30 ppm by weight and especially about 50 ppm by weight, based on the amount of the monomers A. For example, the monomer composition can be prepared by using an ethylenically unsaturated monomer A with an appropriate content of hydroquinone monoether. Preferred hydroquinone monoethers are hydroquinone monomethyl ether (MEHQ) and/or alpha-tocopherol (vitamin E).

It has been found to be advantageous when the polymerization is performed in the presence of at least one wetting agent, i.e. the aqueous suspension during the polymerization comprises at least one wetting agent.

Suitable wetting agents are particularly anionic emulsifiers and nonionic emulsifiers.

Typical anionic emulsifiers generally have at least one non-polymerizable, non-functionalized hydrocarbyl radical, for example an alkyl, aryl or aralkyl radical having generally at least 6 carbon atoms, especially at least 8 carbon atoms, and at least one anionic group, especially at least one sulfonate group, phosphonate group, phosphate group or carboxylate group. Preferred non-functionalized hydrocarbyl radicals are alkyl groups having 6 to 22 and especially 8 to 20 carbon atoms, naphthyl, phenyl and $C_4$-$C_{18}$-alkyl-substituted phenyl. Preferred, for neutralization of the anionic groups, the anionic emulsifiers have cations from the group of the alkali metals, especially sodium ions, or ammonium ions ($NH^{4+}$).

Examples of wetting agents from the group of the anionic emulsifiers are Examples of anionic emulsifiers preferred in accordance with the invention are the salts, especially the alkali metal and ammonium salts, of dialkyl esters of sulfosuccinic acid (alkyl radicals: each $C_4$ to $C_{12}$) such as dibutyl sulfosuccinate, dihexyl sulfosuccinate, dioctyl sulfosuccinate, di(2-ethylhexyl) sulfosuccinate or didecyl sulfosuccinate, alkyl sulfates (alkyl radical: $C_8$ to $C_{18}$) such as lauryl sulfate, isotridecyl sulfate or cetyl sulfate, stearyl sulfate;

of sulfuric monoesters of ethoxylated alkanols (EO level: 2 to 30, alkyl radical: $C_{10}$ to $C_{18}$), such as the sulfates of (poly)ethoxylated lauryl alcohol, of (poly)ethoxylated isotridecanol, of (poly)ethoxylated myristyl alcohol, of (poly)ethoxylated cetyl alcohol, of (poly)ethoxylated stearyl alcohol of sulfuric monoesters of ethoxylated alkylphenols (EO level: 2 to 30, alkyl radical: $C_4$ to $C_{18}$), of alkylsulfonic acids (alkyl radical: $C_8$ to $C_{18}$), such as laurylsulfonate and isotridecylsulfonate, of mono-, di- and trialkylarylsulfonic acids (alkyl radical: $C_4$ to $C_{18}$), such as dibutylnaphtylsulfonate, cumylsulfonate, octylbenzenesulfonate, nonylbenzenesulfonate, dodecylbenzenesulfonate and tridecylbenzenesulfonate, of sulfuric monoesters of di- or tristyrylphenol ethoxylates (EO level: 2 to 30;

of mono- and diesters of phosphoric acid, including mixtures thereof with the corresponding triesters, especially esters thereof with $C_8$-$C_{22}$-alkanols, (poly)ethoxylated $C_8$-$C_{22}$-alkanols, $C_4$-$C_{22}$-alkylphenols, (poly)ethoxylated $C_4$-$C_{22}$-alkylphenols, or (poly)ethoxylated di- or tristyrylphenols.

Examples of suitable anionic emulsifiers are also the following compounds of the general formula A:

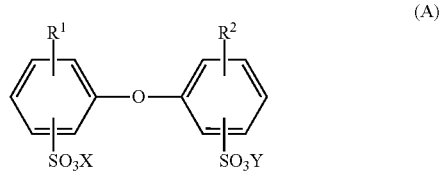

in which $R^1$ and $R^2$ are each hydrogen or $C_4$-$C_{14}$-alkyl and are not both hydrogen, and X and Y are suitable cations, e.g. alkali metal ions and/or ammonium ions. Preferably, $R^1$ and $R^2$ are each hydrogen or linear or branched alkyl radicals having 6 to 18 carbon atoms and especially having 6, 12 or 16 carbon atoms, where $R^1$ and $R^2$ are not both simultaneously hydrogen. X and Y are preferably each sodium, potassium or ammonium ions, particular preference being given to sodium. Particularly advantageous compounds are those in which X and Y are each sodium, $R^1$ is a branched alkyl radical having 12 carbon atoms and $R^2$ is hydrogen or has one of the definitions specified for $R^1$ other than hydrogen. Frequently, technical grade mixtures having a proportion of 50 to 90% by weight of the monoalkylated product are used, for example Dowfax® 2A1 (trademark of Dow Chemical Company).

Typical nonionic emulsifiers generally have at least one non-polymerizable, non-functionalized hydrocarbyl radical, for example an alkyl, aryl or aralkyl radical having generally at least 6 carbon atoms, especially at least 8 carbon atoms, and at least one hydrophilic nonionic group, for example at least one oligo-$C_2$-$C_3$-alkylene oxide group, especially an oligoethylene oxide group or oligo-ethylene oxide-co-propylene oxide group, or a mono- or oligosaccharide group. Preferred non-functionalized hydrocarbyl radicals are alkyl groups having 6 to 36 and especially 8 to 24 carbon atoms, naphthyl, phenyl and $C_4$-$C_{18}$-alkylsubstituted phenyl. Preferred hydrophilic nonionic groups are selected from oligo-$C_2$-$C_3$-alkylene oxide groups, especially from oligoethylene oxide groups. Preferred oligo-$C_2$-$C_3$-alkylene oxide groups, especially oligoethylene oxide groups, have typically 3 to 200, particularly 5 to 150 and especially 10 to 100 $C_2$-$C_3$-oxyalkylene repeat units, especially oxyethylene repeat units.

Examples of preferred nonionic emulsifiers are the following emulsifier types:

ethoxylated alkanols having 8 to 36 carbon atoms, especially 10 to 24 carbon atoms, in the alkyl radical, ethoxylated mono-, di- and trialkylphenols having typically 4 to 12 carbon atoms in the alkyl radicals, ethoxylated mono-, di- and tristyrylphenols, $C_6$-$C_{22}$-alkyl (poly)glycosides having 1 to 3 glucose units.

The aforementioned ethoxylated alkanols, ethoxylated alkylphenols and ethoxylated mono-, di- and tristyrylphenols typically have an ethoxylation level in the range from 5 to 150 and especially 10 to 100. Particular preference is given to ethoxylated alkanols having 8 to 36 carbon atoms, especially 10 to 24 carbon atoms, in the alkyl radical and an ethoxylation level in the range from 5 to 150 and especially 10 to 100.

The wetting agent preferably comprises at least one nonionic emulsifier, for example one nonionic emulsifier or two nonionic emulsifiers of different types. More particularly, the wetting agent comprises at least one nonionic emulsifier as a main constituent of the wetting agent. More particularly, the at least one nonionic emulsifier accounts for at least 50% by weight, especially at least 80% by weight, based on the total amount of the wetting agent. Suitable wetting agents are also mixtures of at least one nonionic and at least one anionic emulsifier.

If the wetting agent is used in the process of the invention, preference is given to using the wetting agent in an amount of 0.01 to 5% by weight, particularly in an amount of 0.1 to 3% by weight and especially in an amount of 0.2 to 2% by weight, based on the total amount of monomer composition and substance S.

For polymerization, the constituents of the reaction mixture, i.e. the monomer composition, the substance S and the aqueous liquid, and, optionally, if desired, wetting agent and/or urea, will be combined. The polymerization initiator will be added to the mixture. If required, the mixture will then be heated to the polymerization temperature. It is also possible first to heat the mixture of monomer composition, substance S and aqueous liquid and any wetting agent and/or urea to the desired reaction temperature and to add the polymerization initiator thereto. The sequence of addition of monomer composition, substance S and aqueous liquid, and of any further constituents, is of minor significance. It is also possible first to add only a portion of the monomers and to add the residual amount of the monomers over the course of the polymerization. Preference is given to combining, prior to the polymerization, the majority of the monomers, the substance S, the aqueous liquid and any wetting agent and/or urea.

The temperature required for polymerization naturally depends on the initiator used and is typically in the range from 20 to 100° C., frequently in the range from 60 to 100° C. and especially in the range from 70 to 90° C.

Because of the fact that the monomers A of the monomer composition are at least partly in neutralized, i.e. anionic, form, the aqueous liquid of the suspension comprising the monomer composition and the substance S typically has a pH above pH 3, especially at least pH 3.5, up to weakly alkaline pH values, i.e. the polymerization is effected at these pH values. The pH of the aqueous suspension at the start of the polymerization is preferably in the range from >pH 3 to pH 8, particularly in the range from pH 3.5 to pH 7.5 and especially in the range from pH 4 to pH 7.

The polymerization can be performed as a batchwise process. For this purpose, the constituents of the reaction mixture will typically be mixed in a suitable polymerization vessel, preferably choosing the amount of aqueous liquid such that the mixture has the desired initial viscosity. The polymerization initiator is then added to this mixture and optionally heated to the necessary polymerization temperature. Preference is given to effecting the polymerization with shearing of the reaction mixture, more particularly using a stirrer or kneader.

If the polymerization is performed batchwise, it is beneficial to first initiate the polymerization by heating and shearing of the reaction mixture until the exothermic polymerization reaction starts, which can be observed by a temperature rise. Then the shearing is stopped until the monomer conversion is at least 90%, in particular at least 95% and especially at least 98%. During that time the temperature is preferably kept at a temperature of at least 90° C., in particular at least 95° C. Once, the desired monomer conversion has been achieved, shearing is continued optionally accompanied by heating, preferably to a temperature of at least 90° C., in particular at least 95° C.

The polymerization can also be performed continuously. For this purpose, a mixture of the constituents of the reaction mixture will typically be fed into a reaction zone at polymerization temperature and the initiator fed into this reaction zone. The amount of aqueous liquid in the mixture of the constituents of the reaction mixture is preferably chosen such that the mixture has the desired initial viscosity. The reaction zone is preferably equipped with apparatuses for mixing the constituents. In a preferred configuration of the continuous polymerization, the polymerization is performed in a heatable reaction vessel equipped with a rotating screw, for example a heatable screw extruder.

For performance of the polymerization, exclusion of oxygen is not required. In other words, the polymerization can be performed in the presence of atmospheric oxygen, i.e. under air. However, the polymerization can also be performed with substantial exclusion of oxygen, for example under inert gas.

The polymerization at first gives a water-containing polymer composite material in the form of a swollen gel that comprises a polymer which results from the polymerization of the monomer composition, and the substance S and also water. The substance S is in homogeneously distributed form in a matrix of the polymer formed in the polymerization, which has swollen because of the presence of the water. Investigations indicate that the polymer resulting from the polymerization of the monomer composition is at least partly bonded covalently to the constituents present in the substance S, probably the cellulose molecules, and can thus be regarded as a graft polymer. By drying, the swollen polymer composite material can be converted to a free-flowing powder.

It has been found to be advantageous when urea is incorporated into the polymer during or after the polymerization. This can be effected, for example, by performing the polymerization in the presence of urea and/or treating the polymer composite material obtained in the polymerization with urea, preferably in the swollen state.

It has been found to be particularly advantageous when the majority of urea, particularly at least 80% and of the amount of urea, especially the whole amount, is incorporated into the polymer composite material during the polymerization. This can be simply achieved by adding the urea to the aqueous suspension prior or during the polymerization reaction. Preferably, the majority of urea, particularly at least 80% and of the amount of urea, especially the whole amount, is incorporated into the aqueous suspension prior to the polymerization. If the urea is incorporated into the polymer composite material during polymerization, the amount of urea is generally selected such that the total amount of urea is in the range from 5 to 50% by weight, particularly in the range from 10 to 35% by weight, more particularly in the range from 15 to 30% by weight, and especially in the range from 20 to 25% by weight, based on the total amounts of monomers A and B in the reaction mixture, i.e. in the aqueous suspension of the particulate solid containing the monomer composition M.

In another embodiment, the majority of urea, particularly at least 80% and of the amount of urea, especially the whole amount, is incorporated into the polymer composite material after the polymerization. More particularly, the urea is incorporated into the swollen polymer composite material obtained in the polymerization. In this case, the procedure will preferably be to incorporate an aqueous solution into the swollen polymer composite material obtained in the polymerization, for example by kneading the aqueous urea solution with the swollen polymer composite material obtained in the polymerization. Alternatively, it is also possible to treat the dried polymer with urea.

If the urea is incorporated into the polymer composite material after polymerization, the urea is preferably used in the form of an aqueous solution or suspension, for example with a concentration in the range from 1 to 60% by weight, especially 2 to 50% by weight. The amount of solution is generally in the range from 0.01 to 5 L, especially in the range from 0.1 to 3 L, per kg of solids in the reaction mixture, i.e. based on the total amount of polymer (=monomer composition) and substance S. If the treatment is performed on swollen polymer composite material, it will be preferable to work at relatively high concentrations, for example urea concentrations in the range from 20 to 60% by weight, especially at higher 25 to 50% by weight. If already dried polymer composite material is treated, preference is given to using urea in the form of a dilute aqueous solution having a concentration in the range from 1 to 25% by weight, especially 2 to 20% by weight.

If the urea is incorporated into the polymer composite material after polymerization, the amount of urea is generally selected such that the total amount of urea is in the range from 1 to 30% by weight, frequently in the range from 3 to 15% by weight and especially in the range from 5 to 10% by weight, based on the solids in the reaction mixture.

Because of the fact that the monomer A is used in at least partly neutralized form for polymerization, a subsequent neutralization of the polymer composite obtained in the polymerization can be dispensed with, since the acidic groups present in the polymer are already at least partly in neutralized form. In this context, the neutralization level of the monomers A used corresponds essentially to the neutralization level of the acid groups present in the polymer or polymer composite.

It is also possible to perform a neutralization when the neutralization level of the acid groups present in the polymer or polymer composite is to be increased. For neutralization/hydrolysis, the polymer composite material obtained will generally be treated with an aqueous solution of a base suitable for neutralization or hydrolysis. Typical bases are alkali such as sodium hydroxide or potassium hydroxide, and ammonia. In general, the base is used in the form of an aqueous solution, for example in the form of concentrated ammonia or in the form of a concentrated aqueous solution of the alkali metal hydroxide, for example in the form of a 20 to 70% by weight solution. The amount of base is chosen such that an at least 10% increase (absolute) in the neutralization level of the neutralizable acid groups in the monomers A polymerized into the polymer is ensured. Preference is given to choosing the amount of base such that, at least theoretically, an at least 20%, particularly an at least 30% or an at least 35% or an at least 50% or full neutralization/hydrolysis is ensured, and, more particularly, the neutralization level of the monomers A polymerized into the polymer or of the resultant acid groups present in the polymer is in the range from 20 to 90%, particularly in the range from 30 to 90% or from 30 to 85% and especially in the range from 35 to 80% or from 50 to 80%.

The polymer composite material obtained in the polymerization and any subsequent treatment with urea or base is generally in water-swollen form, i.e. in the form of a swollen hydrogel. To obtain a solid polymer composite material, the swollen gel will typically then be subjected to drying.

The drying can be effected in a manner known per se, for example in suitable driers, for example drying cabinets, paddle driers, belt driers or roll driers. Preference is given to conducting the drying until the content of moisture (water and any solvents) is not more than 20% by weight, particularly not more than 10% by weight, for example down to a residual moisture content of 0.5 to 20% by weight, particularly 1 to 15% by weight and especially 1 to 10% by weight. In this context, it has been found to be advantageous when the drying is at least partly performed at a temperature of at least 80° C., particularly at least 100° C. and especially above 100° C. such as a temperature of at least 110° C., for example at a temperature in the range from 80 to 250° C., particularly in the range from 100 to 220° C. and especially in the range from 110 to 200° C. The drying can be accelerated by applying reduced pressure. The drying time is preferably 0.5 to 2 h.

In a particular embodiment of the invention the drying comprises (i) a first step, where the polymer obtained after the polymerization is subjected to drying at reduced pressure of preferably less than 100 mbar, e.g. from 10 to <100 mbar, and temperatures below 100° C., e.g. at temperatures in the range from 60 to <100° C., and (ii) a subsequent second step where the polymer is dried at temperatures above 100° C., e.g. from >100 to 200° C., in particular from 120 to 150° C. The second step may be performed at ambient or slightly reduced pressure, i.e. in the range from 900 to 1020 mbar, or at reduced pressure and preferably at a pressure in the range from 10 to <900 mbar, in particular from 10 to <200 mbar. The subsequent step ii) may be performed at ambient pressure during the complete drying time or at ambient pressure first followed by drying at reduced pressure. The subsequent step ii) may also be performed at reduced pressure during the complete drying time In another embodiment, the drying is performed by using a belt drier. In this embodiment, drying is preferably performed at a temperature in the range from 120 to 250° C., in particular in the range from 140 to 200° C., especially at 150 to 180° C. and at ambient pressure or slightly reduced pressure, e.g. from 900 to 1020 mbar.

The dried polymer composite material can be ground and classified. Grinding can typically be accomplished using one-stage or multistage roll mills, preferably two or three-stage roll mills, pinned disk mills, hammer mills or vibratory mills. Oversize gel lumps which often still have not dried on the inside are elastomeric and can lead to problems in the grinding, and are therefore preferably removed before the grinding, which can be done in a simple manner by wind sifting or by means of a sieve ("guard sieve" for the mill). In view of the mill used, the mesh size of the sieve should be selected such that a minimum level of disruption resulting from oversize, elastomeric particles occurs.

In this way, the polymer composite material is obtained in the form of a pelletized material, especially of a free-flowing pelletized material.

The polymer composite material obtainable in accordance with the invention is formed from the polymerized monomers of the monomer composition M and the substance S used in the polymerization. If the polymerization has been followed by treatment with urea, it additionally comprises at least a portion of the urea used in the treatment. The weight ratio of polymer (i.e. polymerized monomers M) and the substance S corresponds substantially to the amounts used and is therefore generally in the range from 1:9 to 9:1, preferably in the range from 2:8 to 8:2 and especially in the range from 3:7 to 7:3 or from 1:2 to 2:1, this ratio the proportion of the polymer originating from the monomers A being calculated on the basis of the acidic form used. The polymerized monomers here form a water-swellable polymer matrix in which the substance S is present in finely divided form.

Without being bound to a theory, it is assumed that under the polymerization conditions there is efficient grafting of the polymer network which forms in the polymerization of the monomer composition to the cellulose molecules present in the substance S.

In the polymer composite material obtainable in accordance with the invention, the neutralizable or hydrolyzable groups are at least partly in the form of neutralized acid groups, i.e. in the form of anionic groups, for example in the case of carboxylic acid groups or groups hydrolyzable to carboxylic acid groups (for example nitrile groups) as carboxylate groups. The proportion of the neutralized acid groups in the polymer composite material is preferably at least 20 mol %, particularly at least 30 mol % and especially at least 35 mol %, based on the total amount of all acid groups in the polymerized monomers A and is, for example, in the range from 10 to 100%, frequently in the range from 20 to 90%, particularly in the range from 30 to 85% or from 30 to 90 and especially in the range from 35 to 80% or from 50 to 80%.

The polymer composites obtainable in accordance with the invention feature good water absorption capacity and good water retention capacity. In general, the water absorption capacity is at least 20 g, particularly at least 40 g and especially at least 50 g per g of polymer composite, calculated as oven-dry material (dry weight). Frequently, the water absorption capacity is in the range from 20 to 500 g per g of polymer (dry weight), particularly 40 to 400 g per g of polymer composite (dry weight) and especially 50 to 300 g per g of polymer composite (dry weight). The water absorption capacity is the amount of tap water of hardness dH°=4 that the polymer absorbs at 22° C. The water absorption capacity can be determined in a manner known per se, for example as the centrifuge retention capacity in analogy to the standard test method No. WSP 241.5-02 "Centrifuge retention capacity" as described in: "Standard Test Methods for the Nonwovens Industry", 2005 edition, published jointly by the Worldwide Strategic Partners EDANA (European Disposables and Nonwovens Association, Avenue Eugène Plasky, 157, 1030 Brussels, Belgium, www.edana.org) and INDA (Association of the Nonwoven Fabrics Industry, 1100 Crescent Green, Suite 115, Cary, N.C. 27518, U.S.A., www.inda.org).

With regard to use, the polymer composite material is preferably provided in the form of a free-flowing pelletized material. In such pelletized materials, the mean particle size of the polymer composite particles is generally at least 200 µm, preferably at least 250 µm and more preferably at least 300 μm, and generally at most 2000 μm, particularly at most 1500 μm and especially at most 1000 μm. The proportion of particles with a particle size of at least 150 μm is generally at least 90% by weight, preferably at least 95% by weight and more preferably at least 98% by weight. The proportion of particles with a particle size of at most 3000 μm is generally at least 90% by weight, preferably at least 95% by weight and more preferably at least 98% by weight. The particle size distribution and mean particle size of the pelletized materials can be determined by the standard test method No. WSP 220.2-05 "Particle size distribution".

Because of their ability to bind and store large amounts of water while at the same time having high compostability, the inventive polymer composites are suitable for a multitude of applications which likewise form part of the subject matter of the invention.

The inventive polymers can advantageously be used for controlled release of liquids, especially water and aqueous solutions, dispersions and emulsions.

More particularly, the inventive polymers are suitable for improving soil qualities, especially in commercial plant growing. To improve the soil quality, the inventive polymers will typically be incorporated into the soil surfaces in application rates of 1 to 1000 kg/ha, especially in an amount of 1 to 25 kg/ha, or in an amount of 0.1 to 100 kg/tonne of soil mass. In this context, the inventive polymers are suitable for improving the quality of plant soil, garden soil, of meadow, lawn and forest soil, or of field soil or field areas. The improved soil quality generally leads to better vigor of the plants, for example improved root growth, such that the plants are more stable and better protected against climatic stress. The inventive polymers are especially suitable for retaining and storing moisture in cultivation areas for crop plants. The inventive polymers are additionally particularly suitable for production of crop soils and for recultivation of areas that have become infertile.

The inventive polymers can additionally be used as a soil additive for dust reduction, for example in riding arenas or in animal stalls. The inventive polymers can additionally be used as a binder in green surfacing, for example of roadsides, slopes, paths and squares, and roof greening. The inventive polymers can be used for binding of animal excrement and unpleasant odors, for example in animal stalls.

The inventive polymer composites can additionally be used as a carrier substance for soil structure improvers, as a carrier substance for soil looseners, as a carrier substance for biologically active substances and active ingredients such as crop protection compositions, minerals, fertilizers, and especially for the controlled release of these substances.

The invention further provides for the use of the inventive polymer composites as an extinguishant additive in firefighting.

The invention further provides for the use of the inventive polymer composites for production of compostable or dissolvable flower or plant vessels, and to the use of the use of the inventive polymers as plant substrates.

The invention further provides for the use of the inventive polymer composites for production of hygiene articles. Inventive hygiene articles are, for example, those intended for use in the case of light or heavy incontinence, for instance pads for heavy or light incontinence, incontinence pants, and additionally diapers, so-called "training pants" for babies and infants, or else feminine hygiene articles such as pads, sanitary napkins or tampons. Such hygiene articles are known. The inventive hygiene articles differ from known hygiene articles in that they comprise at least one inventive polymer composite material. Also found has been a process for producing hygiene articles, which comprises using, in the production of the hygiene article in question, at least one inventive polymer composite material in place of or together with a superabsorbent. In addition, processes for producing hygiene articles using superabsorbents are known. The hygiene articles also include training pants for children, shoe insoles and other hygiene articles for absorption of body fluids.

The inventive polymer composites can also be used in many fields of industry in which fluids or liquids, especially water or aqueous solutions, are absorbed. These fields are, aside from hygiene articles such as diapers for babies and small children, incontinence pads, sanitary napkins, tampons and the like, for example, storage, packaging, transport (as constituents of packaging material for water- or moisture-sensitive articles, for instance for flower transport, and also as protection against mechanical effects); animal hygiene (in cat litter); food packaging (transport of fish, fresh meat; absorption of water, blood in fresh fish or meat packaging); medicine (wound plasters, water-absorbing material for burn dressings or for other weeping wounds), cosmetics (carrier material for pharmaceutical chemicals and medicaments, rheumatic plasters, ultrasonic gel, cooling gel, cosmetic thickeners, sunscreen); thickeners for oil/water or water/oil emulsions; textiles (moisture regulation in textiles, shoe insoles, for evaporative cooling, for instance in protective clothing, gloves, headbands); chemical engineering applications (as a catalyst for organic reactions, for immobilization of large functional molecules such as enzymes, as an adhesive in agglomerations, heat stores, filtration aids, hydrophilic components in polymer laminates, dispersants, liquefiers); as assistants in powder injection molding, in the building and construction industry (installation, in loam-based renders, as a vibration-inhibiting medium, assistants in tunnel excavations in water-rich ground, cable sheathing); water treatment, waste treatment, water removal (deicers, reusable sand bags); cleaning; agrochemical industry (irrigation, retention of melt water and dew deposits, composting additive, protection of forests from fungal/insect infestation, retarded release of active ingredients to plants); for firefighting or for fire protection; coextrusion agents in thermoplastic polymers (for example for hydrophilization of multilayer films); production of films and thermoplastic moldings which can absorb water (e.g. films which store rain and dew for agriculture; films comprising polycomposite for maintaining freshness of fruit and vegetables which are packaged in moist films; polycomposite-polystyrene coextrudates, for example for packaging foods such as meat, fish, poultry, fruit and vegetables); or as a carrier substance in active ingredient formulations (pharmaceuticals, crop protection).

I. TEST METHODS

The composite material is tested by the test methods described below.

The standard test methods described hereinafter and designated "WSP" are described in: "Standard Test Methods for the Nonwovens Industry", 2005 edition, published jointly by the Worldwide Strategic Partners EDANA (European Disposables and Nonwovens Association, Avenue Eugene Plasky, 157, 1030 Brussels, Belgium, www.edana.org) and INDA (Association of the Nonwoven Fabrics Industry, 1100 Crescent Green, Suite 115, Cary, N.C. 27518, U.S.A., www.inda.org). This publication is available both from EDANA and from INDA.

All measurements described below should, unless stated otherwise, be conducted at an ambient temperature of 23±2° C. and a relative air humidity of 50±10%. The superabsorbent particles are mixed thoroughly before the measurement unless stated otherwise.

Centrifuge Retention Capacity (CRC)

The centrifuge retention capacity of the superabsorbent is determined by the standard test method No. WSP 241.5-02 "Centrifuge retention capacity".

Absorbency Under a Load of 0.3 psi (AUL 0.3 psi)

The absorbency under a load of 2068 Pa (0.3 psi) of the superabsorbent is determined by the standard test method No. WSP 242.2-05 "Absorption under pressure".

Absorbency Under a Load of 0.7 psi (AUL 0.7 psi)

The absorbency under a load of 4826 Pa (0.7 psi) of the superabsorbent is determined analogously to the standard test method No. WSP 242.2-05 "Absorption under pressure", except using a weight of 49 g/cm² (leads to a load of 0.7 psi) instead of a weight of 21 g/cm² (leads to a load of 0.3 psi).

Moisture Content of the Superabsorbent (Residual Moisture, Water Content)

The water content of the superabsorbent particles is determined by the standard test method No. WSP 230.2-05 "Moisture content".

Mean Particle Size

The mean particle size of the polymer composite particles is determined by the standard test method No. WSP 220.2-05 "Particle size distribution".

Residual Monomer Content:

The residual monomer content of the polymer composite particles is determined by the standard test method No. WSP 210.2-05 "Residual Monomers".

The content of soluble compounds containing carboxyl groups in the polymer composites produced was conducted with the aid of the edana standard test WSP 270.3 (10).

The free swellability or absorption capacity of the polymer composites produced was determined as follows (edana standard test WSP 240.3 (10)-ISO 3696:1987—Grade 3).

II. PREPARATION EXAMPLES

Elucidation of Trade Names

Lutensol® AT 80: ethoxylated $C_{16}$-$C_{18}$ fatty alcohol with about 80 ethylene oxide units (BASF SE), Laromer® PO 9044: Triacrylate of ethoxylated glycerol having with about 3 ethylene oxide units (BASF SE)

ARBOCEL® BC 1000: ground cellulose having a maximum fiber length of 0.7 cm (Rettenmeier Holding AG), Further feedstocks used:

Flax dust: conventional flax dust having the following grain distribution: 2% by weight >600 µm; 73% by weight 50-600 µm; 25% by weight <50 µm.

Solution A: aqueous solution of the following composition 1000 µM Ca, 2000 µM $NO_3$, 200 µM $NH_4$, 651 µM $SO_4$, 850 µM K, 325 µM Mg, 300 µM Cl, 100 µM $PO_4$, 8 µM B, 1 µM Mn, 0.2 µM Cu, 0.2 µM Zn and 0.2 µM Mo. Solution A was used to determine the free swellability or absorption capacity of the polymers produced by means of the above-specified method.

Example 1

The reaction which follows was performed under protective gas atmosphere and all the starting materials mentioned were purged in a nitrogen stream before addition:

28.4 g of acrylic acid, 0.43 g of methylenebisacrylamide, 104.42 g of 37.5% sodium acrylate solution and 213.83 g of water were blended in a 1 L reaction vessel. This was followed by the addition of 2.0 g of a 20% solution of Lutensol® AT 80 in 1.6 g of acrylic acid, and also 30 g of flax dust and 10 g of ARBOCEL® BC 1000. All constituents were mixed vigorously to give a homogeneous mass. After the addition of 2×2 g of a 10% aqueous ammonium peroxodisulfate solution in portions and repeated stirring, the reaction mixture was heated at external temperature of 95° C. while stirring. After 25 min, the reaction mixture had attained the maximum temperature of 72° C. The soft elastic gel obtained was dried at 155° C. for 90 min and then mechanically comminuted. The pale brown, free-flowing solid thus obtained showed, together with deionized water or solution A at room temperature, the following free swellability or absorption capacity per g of solids as a function of time:

|  | 2 h | 24 h | 72 h | 168 h |
| --- | --- | --- | --- | --- |
| Solution A | 76.4 | 76.8 | 73.5 | 74.2 |
| Water | 132.8 | 151.2 | 163.7 | 155.0 |

The solid produced comprised 39987 ppm of residual acrylic acid and 15.2% soluble components containing carboxyl groups.

Example 2

The process according to example 2 was repeated, except that the addition of the 10% aqueous ammonium peroxodisulfate solution was followed by additional addition of 1.0 g of a 0.245% aqueous hydrogen peroxide solution and 1.0 g of a 5.67% aqueous ascorbic acid solution while stirring. Without external heat supply, the reaction mixture attained the maximum temperature of 30.4° C. after 38 min.

The pale brown, free-flowing solid thus obtained showed, together with deionized water or solution A at room temperature, the following free swellability or absorption capacity per g of solids as a function of time:

|  | 2 h | 24 h | 72 h | 168 h |
| --- | --- | --- | --- | --- |
| Solution A | 73.6 | 71.7 | 62.9 | 55.5 |
| Water | 92.6 | 99.2 | 96.4 | 102.7 |

The solid produced comprised 1755 ppm of residual acrylic acid and 1.15% soluble components containing carboxyl groups.

Example 3

The process according to example 2 was repeated, but the material obtained after the drying was thermally aftertreated at 155° C. for 1 h.

The solid thus produced comprised 2328 ppm of residual acrylic acid.

Example 4

The process according to example 1 was repeated, except that 23.4 g of acrylic acid, 0.36 g of methylenebisacrylamide, 87.5 g of 37.5% sodium acrylate solution, 222 g of water, 37.5 g of flax dust, 12.5 g of ARBOCEL® BC 1000 and 1.0 g of the 10% aqueous ammonium peroxodisulfate solution were used. After 30 min, the reaction mixture attained a temperature of 30.0° C. This was followed by heating at external temperature of 95° C. with stirring for 1 h, in the course of which the reaction mixture attained the maximum temperature of 73.6° C. after 53 min.

The pale brown, free-flowing solid thus obtained showed, together with deionized water or solution A at room temperature, the following free swellability or absorption capacity per g of solids as a function of time:

|  | 2 h | 24 h | 72 h | 168 h |
| --- | --- | --- | --- | --- |
| Solution A | 37.5 | 40.9 | 31.2 | 27.7 |
| Water | 66.2 | 80.1 | 81.1 | 83.6 |

The solid produced comprised 60 016 ppm of residual acrylic acid and 15.8% soluble components containing carboxyl groups.

Example 5

The process according to example 4 was repeated, except that the soft elastic gel obtained was dried at 40° C. under reduced pressure for 48 h.

The pale brown, free-flowing solid thus obtained showed, together with deionized water or solution A at room temperature, the following free swellability or absorption capacity per g of solids as a function of time:

|  | 2 h | 24 h | 72 h | 168 h |
| --- | --- | --- | --- | --- |
| Solution A | 67.3 | 63.2 | 41.5 | 35.7 |
| Water | 127.6 | 213.3 | 227.6 | 243.8 |

The solid produced comprised 96 821 ppm of residual acrylic acid and 23.2% soluble components containing carboxyl groups.

Example 6

The reaction which follows was performed under protective gas atmosphere and all the starting materials mentioned were purged in a nitrogen stream before addition:

A kneader was charged with 897 g of flax dust and 299 g of ARBOCEL® BC 1000. Subsequently, the kneader was put into operation, and a solution of 897 g of acrylic acid and 12.86 g of methylenebisacrylamide, 3147.46 g of 37.2% sodium acrylate solution and 930.15 g of deionized water were added and blended together stepwise. Thereafter, 119.6 g of a 10% aqueous solution of Lutensol® AT 80 were added and kneaded in. After a solution of 3.15 g of sodium peroxodisulfate, 0.985 g of 30% hydrogen peroxide solution, 10 g of water and 0.3594 g of ascorbic acid in 10 g of water had been added and the temperature of the reaction mixture began to rise, it was heated to 80° C. and this temperature was maintained for 1 h.

The soft elastic gel obtained was dried at 85° C. for 1 h and at 150° C. for 1 h and then comminuted.

The pale brown, free-flowing solid thus obtained showed, together with deionized water or solution A at room temperature, the following free swellability or absorption capacity per g of solids as a function of time:

|  | 2 h | 24 h | 168 h |
| --- | --- | --- | --- |
| Solution A | 51.1 | 26.4 | 15.7 |
| Water | 70.0 | 72.4 | 78.4 |

The solid produced comprised 52 519 ppm of residual acrylic acid and 9.7% soluble components containing carboxyl groups.

Example 7

The process according to example 4 was repeated, except that a solution of 64.29 g of urea in 1000 g of deionized water per kg of solids was then added and the mixture was then kneaded for 1 h. The soft elastic gel obtained was dried at 150° C. for 1 h and then comminuted.

The solid thus produced comprised 15 149 ppm of residual acrylic acid and 11.3% soluble components containing carboxyl groups. The water absorption capacity after 7 days was 59.5 g per g of solids and the absorption capacity of solution A was 29.6 g per g of solids.

Example 8

The process according to example 4 was repeated, except that 37.5 g of deionized water and a solution of 2.4 g of urea in 1000 g of deionized water per 35.9 g of solids were then added and the mixture was then kneaded for 30 min. The soft elastic gel obtained was dried at 60° C. under reduced pressure for 24 h and then comminuted. The solid thus produced comprised 36 530 ppm of residual acrylic acid.

Example 9

The process according to example 6 was repeated, except that the soft elastic gel obtained was dried at 150° C. for 1 h and then comminuted. The solid thus produced comprised 11 411 ppm of residual acrylic acid. The water absorption capacity after 7 days was 60.3 g per g of solids and the absorption capacity of solution A was 35.4 g per g of solids.

The following example 10 was performed in a Drais 1200 ploughshare mixer with 8 ploughshares having a cylindrical geometry and an internal volume of 1000 l.

Example 10

32.6 kg of urea, 0.77 kg Lutensol® AT 80 and 97.8 kg of distilled water were mixed together. The mixture is called solution 1.

0.836 kg of N,N'-methylenebis(acrylamide) and 58.23 kg of acrylic acid were mixed together and this mixture is then called solution 2.

The mixer was first filled 116.4 kg of flax dust, solution 1, 255.0 kg of a potassium acrylate solution (35 weight % in water) and finally with the solution 2. The mixer was set to maximum speed (90 rpm) and the mixture stirred for 30 minutes. Afterwards a mixture of 1.17 kg sodium persulfate with 10.5 kg of distilled water and 0.35 kg 2,2'-azobis[2-(2-imidazolin-2-yl)propane]dihydrochloride with 23.76 kg distilled water was filled into the mixer. The oil temperature of the mixer was set to 120° C. and the reaction mixture was heated to 60° C. At 60° C. the mixer was stopped and held for three hours. After three hours the mixer was set again to maximum speed and the obtained polymer gel was dried under vacuum (<100 mbar) until reaching 20% residual moisture.

Drying was then continued under normal pressure conditions at a temperature of 110 to 120° C. using a stream of dry nitrogen of 2 m³/h. After reaching 6% residual moisture the drying was continued for one hour at vacuum (<100 mbar) at a temperature of about 100 to 110° C.

258 kg final material was obtained as a pale brown powder with a residual acrylic acid content of 610 ppm and 15.3% extractable content. The obtained material showed the following free swellability or absorption capacity per g of solids as a function of time and the following CRC.

|  | Free Swellability [g/g] | | | | CRC |
|---|---|---|---|---|---|
|  | 2 h | 24 h | 48 h | 168 h | [g/g] |
| Solution A | 59.4 | 39.3 | 25.2 | 16.5 | 5.9 |
| Water | 79.0 | 87.9 | 90.9 | 97.5 | 43.6 |

Example 11

An IKA laboratory kneader was heated to 80° C. and 38.8 g of flax dust were filled inside during maximum mixing speed. During this time the reactor was flushed for 30 minutes with 200 l/h $CO_2$.

A monomer solution containing 16.9 g of acrylic acid, 2.79 g of 10% solution of N,N'-methylenebis(acrylamide) in acrylic acid, 85.1 g of a 35% aqueous potassium acrylate solution, 2.56 g of a 10% aqueous solution of Lutensol AT 80, 43.3 g of a 25% aqueous solution of urea and 7.5 g distilled water was prepared by mixing and the solution was flushed for 30 minutes with 200 l/h nitrogen.

The monomer solution was put into the kneader with the flax dust and mixed at 80° C. to obtain a homogenous mixture. Then, 1.94 g of a 20% aqueous sodium persulfate solution and 1.17 g of a 10% aqueous solution of 2,2'-azobis[2-(2-imidazolin-2-yl)propane]dihydrochloride were added to the reactor. After 60 minutes of polymerization at 80° C., the reactor was cooled down to 40° C. The obtained polymer gel was cut into small pieces and dried for 60 minutes at 150° C.

80 g final material was obtained as a pale brown powder with a residual acrylic acid content of 8100 ppm and 14.1% extractable content.

Example 12

An IKA laboratory kneader was heated to 80° C. and 38.8 g of flax dust were filled inside during maximum mixing speed. During this time the reactor was flushed for 30 minutes with 200 l/h $CO_2$.

A monomer solution containing: 16.9 g of acrylic acid, 2.79 g of 10% solution of N,N'-methylenebis(acrylamide) in acrylic acid, 85.1 g of a 35% aqueous solution of potassium acrylate, 2.56 g of a 10% aqueous solution of Lutensol AT 80, 43.3 g of a 25% aqueous solution of urea, 5.8 g distilled water was prepared by mixing and the solution was flushed for 30 minutes with 200 l/h nitrogen.

The monomer solution was put into the kneader with the flax dust and mixed at 80° C. to obtain a homogenous mixture. Then, 1.94 g of a 20% aqueous solution of sodium persulfate, 1.17 g of a 2% aqueous solution of hydrogen peroxide, 1.56 g of a 2% aqueous solution ascorbic acid were added to the reactor. After 90 minutes of polymerization at 80° C., the reactor was cooled down to 40° C. The obtained polymer gel was cut into small pieces and dried for 60 minutes at 150° C.

82 g final material was obtained as a pale brown powder with a residual acrylic acid content of 12000 ppm and 17.5% extractable content. The obtained material showed the following free swellability or absorption capacity per g of solids as a function of time and the following CRC.

|  | Free Swellability [g/g] | | | | CRC |
|---|---|---|---|---|---|
|  | 2 h | 24 h | 48 h | 168 h | [g/g] |
| Solution A | 53.1 | 19.1 | 9.6 | 7.3 | 2.3 |
| Water | 77.3 | 81.4 | 80.7 | 84.6 | 37.1 |

Example 13

An IKA laboratory kneader was heated to 80° C. and 38.8 g of flax dust were filled inside during maximum mixing speed. During this time the reactor was flushed for 30 minutes with 200 l/h $CO_2$.

A monomer solution containing: 16.6 g of acrylic acid, 3.11 g of 10% solution of Laromer® PO 9044 in acrylic acid, 85.0 g of a 35% aqueous solution of potassium acrylate, 2.56 g of a 10% aqueous solution of Lutensol AT 80, 43.3 g of a 25% aqueous solution of urea, 5.9 g distilled water was prepared by mixing and the solution was flushed for 30 minutes with 200 l/h nitrogen.

The monomer solution was put into the kneader with the flax dust and mixed at 80° C. to obtain a homogenous mixture. Then, 1.94 g of a 20% aqueous solution of sodium persulfate, 1.17 g of a 2% aqueous solution of hydrogen peroxide, 1.56 g of a 2% aqueous solution of ascorbic acid was added to the reactor. After 90 minutes of polymerization at 80° C., the reactor was cooled down to 40° C. The obtained polymer gel was cut into small pieces and dried for 60 minutes at 150° C.

78 g final material was obtained as a pale brown powder with a residual acrylic acid content of 7100 ppm and 20.2% extractable content. The obtained material showed the following free swellability or absorption capacity per g of solids as a function of time and the following CRC.

|  | Free Swellability [g/g] | | | | CRC |
|---|---|---|---|---|---|
|  | 2 h | 24 h | 48 h | 168 h | [g/g] |
| Solution A | 67.0 | 24.0 | 20.1 | 14.8 | 4.4 |
| Water | 116.5 | 121.8 | 121.1 | 127.6 | 67.1 |

Example 14

An IKA laboratory kneader was heated to 80° C. and 38.9 g of flax dust were filled inside during maximum mixing speed. During this time the reactor was flushed for 30 minutes with 200 l/h $CO_2$.

A monomer solution containing: 16.7 g of acrylic acid, 3.11 g of 10% solution of Laromer® PO 9044 in acrylic acid, 85.3 g of a 35% aqueous potassium acrylate solution, 43.4 g of a 25% aqueous solution of Urea, 7.9 g distilled water was prepared by mixing and the solution was flushed for 30 minutes with 200 l/h nitrogen.

The monomer solution was put into the kneader with the flax dust and mixed at 80° C. to obtain a homogenous mixture. Then, 1.95 g of a 20% aqueous solution of sodium persulfate, 1.17 g of a 2% aqueous solution of hydrogen peroxide, 1.56 g of a 2% aqueous solution of ascorbic acid was added to the reactor. After 90 minutes of polymerization at 80° C., the reactor was cooled down to 40° C. The obtained polymer gel was cut into small pieces and dried for 60 minutes at 150° C.

75 g final material was obtained as a pale brown powder with a residual acrylic acid content of 7300 ppm and 19.5% extractable content. The obtained material showed the following free swellability or absorption capacity per g of solids as a function of time and the following CRC.

|  | Free Swellability [g/g] | | | | CRC |
|---|---|---|---|---|---|
|  | 2 h | 24 h | 48 h | 168 h | [g/g] |
| Solution A | 61.4 | 19.2 | 14.8 | 12.4 | 3.9 |
| Water | 104.5 | 112.4 | 111.2 | 113.7 | 55.4 |

III. STUDY OF GROWTH-PROMOTING ACTION

With the aid of the test described hereinafter, the effects of the inventive polymers on the shoot and root growth of corn plants were studied.

The polymer to be studied (0.01-10 g/kg) was added to a water-moistened plant substrate and mixed in until homogeneously distributed. To determine the blank value, correspondingly moistened quartz sand was used. Then five precultivated corn seedlings were planted into each pretreated substrate and cultivated at ambient temperature for about 3 weeks, in the course of which the plants were watered with a compound fertilizer solution once per week. The plants were removed from the pots along with the roots, the roots were cleaned by washing and the plants were assessed for appearance and size. Then the shoot and root were separated from each other in each case and both parts were weighed to determine their fresh weight. The shoots and roots were subsequently dried to constant weight and their dry weights were determined. The final weights for the shoots and roots of 5 identically treated plants in each case were used to calculate the mean values for fresh and dry weights. In this test, for the polymer composites of examples 1, 3, 5, 6, 7, 10 and to 11, an improvement in the shoot and root growth was found.

| Example | Mass increase of fresh weight [%] compared to untreated sample | | Mass increase of dry weight [%] compared to untreated sample | |
|---|---|---|---|---|
|  | Shoot | Root | Shoot | Root |
| 1 | 32.7 | 51.6 | 32.1 | 53.8 |
| 2 | 24.4 | 65.4 | 31.2 | 48.4 |
| 3 | 14.3 | 46.9 | 14.7 | 32.6 |
| 4 | 36.6 | 53.9 | 67.0 | 21.5 |
| 5 | 11.6 | 31.8 | — | 72.0 |
| 8 | 42.8 | 35.4 | 45.7 | 39.7 |
| 9 | 69.3 | 45.9 | 67.7 | 65.9 |

The invention claimed is:

1. A process for producing polymer composites suitable for absorbing and storing aqueous liquids, comprising:
   a free-radical polymerization of a monomer composition M which comprises
   a) 50 to 100% by weight, based on the total amount of monomers A and B, of at least one monomer A having one ethylenic double bond and at least one neutralizable acid group,
   b) 0 to 50% by weight of optionally one or more comonomers B which are different than the monomers A and have one ethylenic double bond, and
   c) 0 to 10% by weight, based on the total amount of monomers A and B, of at least one crosslinker C,
   in an aqueous suspension of a water-insoluble particulate substance S comprising cellulose or lignocellulose, the weight ratio of the monomer composition M to the substance S being in the range from 9:1 to 1:9;
   wherein the monomers A used for polymerization are present in the aqueous suspension in anionic form to an extent of at least 10 mol %; and
   wherein the aqueous suspension contains urea during the polymerization.

2. The process of claim 1, wherein the monomer A used for polymerization is present in the aqueous suspension in anionic form to an extent of 30 to 80 mol %.

3. The process of claim 1 wherein the amount of urea is from 5 to 50% by weight, based on the total amount of monomers A and B.

4. The process of claim 1, wherein the particulate substance S comprises a lignocellulose material.

5. The process of claim 4, wherein the substance S is selected to an extent of at least 50% by weight, based on the total amount of substance S, from hemp dust, flax dust, sawdust, bran, ground straw, ground olive stones, ground tree bark, reject material from pulp production, sugar beet peel, sugar cane waste, rice husks, cereal husks, ground hemp fibers, ground flax fibers, ground Chinese silvergrass fibers, ground coconut fibers, ground kenaf fibers or ground wood fibers, and wastes from biogas production.

6. The process of claim 1, wherein the weight ratio of particulate substance S and of the total amount of monomers in the monomer composition M is from 1:9 to 9:1.

7. The process of claim 1, wherein at least 90% by weight of the substance S has maximum particle dimensions below 1000 μm, determined by sieve analysis.

8. The process of claim 1, wherein the monomers A are selected from monoethylenically unsaturated $C_3$-$C_8$-monocarboxylic acids, mixtures thereof and mixtures of at least one monoethylenically unsaturated $C_3$-$C_8$-monocarboxylic acid with one or more monoethylenically unsaturated $C_4$-$C_8$-dicarboxylic acids.

9. The process of claim 1, wherein the monomers A account for at least 90% by weight, based on the total amount of monomers A and B.

10. The process of claim 1, wherein the monomer composition comprises at least one crosslinker C having at least two ethylenically unsaturated groups.

11. The process of claim 1, wherein the aqueous suspension comprises at least two different polymerization initiators.

12. The process of claim 11, wherein the aqueous suspension comprises a first polymerization initiator which is selected from the group consisting of azo-initiators and redox-initiators and a second initiator, which is selected from the salts of peroxodisulfuric acid.

13. The process of claim 1, wherein the polymer after the polymerization is subjected to a drying step.

14. The process of claim 13, wherein the drying step comprises (i) a first step, where the polymer obtained after the polymerization is subjected to drying at reduced pressure of less than 100 mbar and temperatures below 100° C. and (ii) a subsequent second step where the polymer is dried at temperatures above 100° C.

* * * * *